(12) United States Patent
Borbely et al.

(10) Patent No.: US 7,879,818 B2
(45) Date of Patent: Feb. 1, 2011

(54) HYALURONIC ACID-BASED CROSS-LINKED NANOPARTICLES

(76) Inventors: Janos Borbely, Kiserdo u. 4, H-4225 Debrecen (HU); Tunde Rente, Huszoles u. 93., H-5350 Tiszafured (HU); Magdolna Bodnar, Luther M. 27., H-4220 Hajduboszormeny (HU); Ildiko Schriffertne Denyicska, Egressy Beni Ter 11., H-4031 Debrecen (HU)

( * ) Notice: Subject to any disclaimer, the term of this patent is extended or adjusted under 35 U.S.C. 154(b) by 0 days.

(21) Appl. No.: 11/645,094

(22) Filed: Dec. 22, 2006

(65) Prior Publication Data

US 2007/0224277 A1 Sep. 27, 2007

Related U.S. Application Data

(60) Provisional application No. 60/754,012, filed on Dec. 23, 2005.

(51) Int. Cl.
*A61K 31/715* (2006.01)
(52) U.S. Cl. .................. 514/54; 424/9.34; 424/489; 424/499; 536/53; 977/906; 977/707; 977/788
(58) Field of Classification Search ............... 424/9.34, 424/489, 499; 514/54; 536/53; 977/906, 977/707, 788
See application file for complete search history.

(56) References Cited

U.S. PATENT DOCUMENTS 6,831,172 B1 * 12/2004 Barbucci et al. .............. 536/53
2006/0040892 A1 * 2/2006 Hu et al. ....................... 514/54

* cited by examiner

*Primary Examiner*—Daniel M Sullivan
*Assistant Examiner*—Sudhakar Katakam
(74) *Attorney, Agent, or Firm*—Thomas A. O'Rourke; Bouner & O'Rourke, LLP

(57) ABSTRACT

Methods are disclosed for preparing novel biodegradable cross-linked nanoparticles based on covalently cross-linking modifications of hyaluronic acid. The final products of the present invention are stable in aqueous media, and may be used as detergents and as additives for pharmaceutical compositions for drug delivery, DNA carrier system and other applications. The nanoparticles made from the biopolymers of the present invention may also be used in controlled release applications, super-absorbent materials as well as biomaterials like enzyme immobilization.

24 Claims, No Drawings

HYALURONIC ACID-BASED CROSS-LINKED NANOPARTICLES

This application claims priority on U.S. Provisional Patent Application Ser. No. 60/754,012, filed Dec. 23, 2005, the disclosures of which are incorporated herein by reference.

FIELD OF THE INVENTION

The present invention relates to the formation of hyaluronic acid-based cross-linked nanoparticles, and especially relates to compositions comprising nano-sized hyaluronic acid that have been amidized with amino groups or esterified with one or more hydroxylic groups. The amount of crosslinking can increased by using carbodiimide (CDI) in the reaction with the hyaluronic acid.

BACKGROUND OF THE INVENTION

Biomaterials made from polymers are being extensively applied in medicine and biotechnology, as well as in other industries. Applications include use as supporting materials, drug-delivery systems with different routes of administration and design, carriers of immobilized enzymes and cells, and materials for orthopedic applications.

Hyaluronic acid (HA) is a naturally occurring biopolymer, which serves important biological functions in bacteria and higher animals including humans. Naturally occurring HA may be found in the tissue of higher animals, in particular as intercellular space filler. It is found in greatest concentrations in the vitreous humour of the eye and in the synovial fluid of articular joints. In gram positive streptococci it appears as a mucoid capsule surrounding the bacterium.

Hyaluronic acid (HA) is a linear polysaccharide consisting of alternating units of β-1,4-D-glucoronic acid and β-1,3-N-acetyl-D-glucosamine. More particularly, HA is comprised of linear, unbranching, polyanionic disaccharide units consisting of glucuronic acid (GlcUA) an N-acetyl glucosamine (GlcNAc) joined alternately by beta 1-3 and beta 1-4 glycosidic bonds. It is a member of the glycosaminoglycan family which includes chondroitin sulphate, dermatin sulphate and heparin sulphate. Unlike other members of this family, it is not found covalently bound to proteins. Chemically, it is a nonsulfated glycosaminoglycan and occurs primarily in vivo as sodium hyaluronat. It is one of the major components of the extracellular matrix of connective tissues. It is present in synovial fluid of joints, in the vitreous body, in umbilical cord and in scaffolding that comprises cartilage. It plays an important role in many biological processes such as in tissue hydratation, in organization of the extracellular matrix, in lubrication and wound healing.

Hyaluronic acid is native to the body, it is a non-immunogenic, biocompatible, biodegradable and bioactive polysaccharide could be an ideal biomaterial for several biomedical applications, such as tissue engineering, drug- or gene-delivery systems. HA is soluble in water independently on its molecular weight, which typically ranged from $1 \times 10^4$ to $2 \times 10^7$ Da. The high molecular mass of HA indicated, that several depolymerization method have been developed, such as ultrasonic-, oxidative degradation, or acid hydrolysis, for preparing low molecular weight or oligomer HA.

Various methods have been developed for the cross-linking modification of hyaluronic acid, which commonly result in gel or film formation. In the type of covalently cross-linking reactions, cross-linkers are molecules with at least two reactive functional groups that allow the formation of bridges between polymeric chains. The most common cross-linkers of HA are aldehydes, thiols, hydrazides and other agents. Ionic cross-linking reactions with charged ions or molecules have also been employed by using several methods to form hydrogels, films or interpenetrating networks based on hyaluronic acid. Hydrogels have been utilized in a wide range of biomedical application, such as, scaffolds and carriers for drugs and gene, or implants for tissue engineering.

Many recent attempts have been made to create particulate systems based on polysaccharides. Hyaluronan nano- and Microsystems can be prepared in a wide range of methods. The emulsion cross-linking method and the coacervation are performed in emulsion. These processes avoid the use of toxic organic materials as cross-linking agents. The solvent evaporation method can be performed in a w/o emulsion also and the aqueous phase is removed by evaporation at high temperature. Spray-drying is a well-known technique to produce cross-linked suspension. This method is based on drying of finely dispersed droplets of solution in a stream of hot air followed by the addition of a cross-linking agent.

Hyaluronic acid is of increasing interest in drug delivery. It is known, for example, to enhance transport of hydrophilic drugs. It has also reported to be useful in colon- or nasal delivery. Hyaluronic acid is also of current interest as a carrier in gene delivery.

SUMMARY OF THE INVENTION

The present invention relates to formation of stable cross-linked nanoparticles of linear polycarboxylic acid and more preferably hyaluronic acid, especially to nano-sized derivatives. Cross-linked compounds are prepared by chemical modification of hyaluronic acid linear polycarboxylic acid with di-, tri- and polyamine. The hyaluronic acid that may be used as a polycarboxylic acid may differ in molecular weight and may include blends of differing hyaluronic acids.

In one embodiment of the present invention there is a method of forming a crosslinked hyalauronic acid using a di-, tri- and polyamine. This approach typically results in higher crosslinking density due to the high nucleophilic activity of the amine. In this embodiment, CDI is added to a mixture of an aqueous solution of HA and diamine or polyamine. The amine groups react with the carboxyl moiety of HA resulting in a crosslinked structure in the nanoparticles obtained by the reaction.

In a second embodiment of the present invention no amine is added to the hyalauronic acid. In this embodiment, a cross bridge i.e., covalent bond is formed between the hydroxyl groups of HA and the carboxyl groups that are part of HA due to the esterification reaction thereby resulting in the desired nanoparticles. However, in this case due to the lower nucleophilic activity of hydroxyl groups the reaction is much slower and the conversion in this embodiment the crosslink density is generally lower than embodiments using a polyamine. However, this method has an advantage that no amine is required for the reaction.

In the reaction of hyalauronic acid with an amine it is believed that the carboxylic groups of the linear hyaluronic acid macromolecule react with the di/tri/poly amines to form an amide linkage and form an intramolecular bridge. Due to this reaction, the starting coiled hyaluronic acid structure is transformed into a globular spherical nanoparticle. In the reaction, a carbodiimide (CDI) can be added to the reaction mixture. The CDI reacts with water eliminated during formation of the amide linkage between the hyaluronic acid and the amines. CDI acts as a coupling agent, it that it can be used to develop amide linkages between carboxyl and amino groups as well as ester linkages between carboxyl and hydroxyl groups. HA as a polycarboxylic acid has functional hydroxyl groups, which can react with the carboxyl groups of HA inside the chain by using CDI. This method result in a cross-linked nanosystem based on HA without any other molecules.

The hyaluronan compositions formed in accordance with the present invention are in the form of a network of nano-sized, biocompatible and biodegradable, cross-linked particles. These particles can be obtained by reacting hyaluronic acid and at least one amine having at least two amino groups or by reacting carboxyl and hydroxyl groups of HA. Both of these reactions can take place in the presence of CDI. More preferably, the process for the preparation of the nano-sized, biocompatible and biodegradable, cross-linked particles is performed by reacting hyaluronic acid in the presence of a carbodiimide as an activator and for amidizing reaction the amine as cross-linking agent. In one embodiment, the amine that is the cross-linking agent is selected from the group consisting of di-, tri-, or polyamines. The hyaluronic acid may be a natural hyaluronic acid, a synthetic hyaluronic acid or a degraded hyaluronic acid.

The nano-sized particles formed by the reaction have an average diameter ranging from about 20 nm to about 200 nm, as determined by transmission electron microscopic imaging.

DETAILED DESCRIPTION

The starting material of the present invention is hyaluronic acid, a linear polysaccharide having at least alternating units of β-1,4-D-glucoronic acid and β-1,3-N-acetyl-D-glucosamine. Chemically, it is a nonsulfated glycosaminoglycan and occurs primarily in vivo as sodium hyaluronat sodium salt (Mw=15 MDa). The hyaluronic acid was a pharmaceutical product and was used as received without further purification.

Hyaluronic acid was partially amidated by reacting it with di-, tri- or polyamino compounds. Preferred diamino compound, such as:

$NH_2-CH_2-CH_2-(O-CH_2-CH_2)_n-NH_2$ where n=2 to 12

Other preferred diamino or polyamino compounds include:

Aliphatic di/tri/polyamines, such as:

$H_2N-(CH_2)_n-NH_2$ n=0 to 6

Hydroxi-di/tri/polyamines, such as $H_2N-(CH_2)_n-(CHOH)_m-NH_2$ n=0 to 2 and m=0 to 2, such as:
  1,3-diamino-2-hydrohypropane Oxo-di/tri/polyamine, such as:
  1,3-diaminoacetone Aromatic di/tri/polyamine, such as:
  2,5-diaminobenzenesulfonic acid
  3,5-diaminobenzoic acid Aromatic di/tri/polyamine, such as:
  2,6-diaminopyridine
  2,5-diaminopyridine
  2,6-diaminopurine Others, such as:
  Poly-(Ethylenglycol)-Bis-(Carboxymethylether)

EXAMPLE 1

Hyaluronic acid was dissolved in water to produce a solution, concentration was 1 mg/ml. The diamine was added to the solution, and then the pH was adjusted to pH 6.5 with 0.1 M sodium hydroxide solution. One diamine that can be used is ,2'(ethylenedioxy)bis(ethylamine). After the addition of the sodium hydroxide solution water soluble carbodiimide is added dropwise, and the reaction mixture was stirred at 4° C. for 30 min and subsequently at room temperature for 24 h. The solution containing hyaluronan nanoparticles was purified by dialysis for 7 days against distilled water and freeze-dried.

Synthesis of cross-linked hyaluronan nanoparticles with 2,2'(ethylenedioxy)bis(ethylamine) at diverse stoichiometric cross-linking ratios were made according to the described reaction conditions.

EXAMPLE 2

Hyaluronic acid was partially esterified by reacting the carboxyl and hydroxyl groups of HA inside the chain by using CDI. Hyaluronic acid was dissolved in water to produce a solution. The concentration was 1 mg/ml, the pH was adjusted to pH 6.5 with 0.1 M sodium hydroxide solution. CDI was dissolved in water. After the addition of sodium hydroxide solution to the water soluble carbodiimide is added dropwise, the reaction mixture was stirred at 4° C. for 30 min and subsequently at room temperature for 24 h. The solution containing hyaluronan nanoparticles was purified by dialysis for 7 days against distilled water and freeze-dried.

Synthesis of cross-linked hyaluronan nanoparticles with 2,2'(ethylenedioxy)bis(ethylamine) at diverse stoichiometric cross-linking ratios were made according to the described reaction conditions The reaction that is performed determinates the cross-linking of hyaluronic acid. This cross-linking can performed so that there different amounts of cross-linking in the final product, i.e., from 1 to 100% cross-linking. The reaction takes place in water, in the presence of a water soluble carbodiimide (CDI) compound, which preferably is 1-[3-(dimethylamino)propyl]-3-ethylcarbodiimide hydrochloride.

EXAMPLE 3

Degradation of Hyaluronic Acid

Hyaluronic acid sodium salt was dissolved in water to obtained 1% (m/m) solution, and then adjusted to pH 2.0 with 6.0 M hydrochloric acid solution. The degradation was carried out at 70° C. stirring for different hours. After that, the pH of the solution was adjusted to 6.0 with 1.0 M sodium hydroxide solution and added sodium chloride solution to obtain 4% (v/v) solution. The reaction mixture was filtered by using 0.45 μm Sartorius membrane filter for the purification. The degraded hyaluronic acid sodium salt was precipitated by using absolute ethanol in the filtrate. The precipitated hyaluronic acid sodium salt was filtered and washed with absolute ethanol. The degraded hyaluronic acid sodium salt was dried in vacuum.

The molecular weight of hyaluronic acid used varied in the range of 20 kDa and 2.5 Mda. The obtained hyaluronic acid was re-dissolved in water to produce a solution, dialyzed against distilled water for 7 days, and then freeze-dried.

EXAMPLE 4

Partial Cross-Linking of Hyaluronic Acid (25% of the Free Carboxylic Groups are Reacting)

100 mg hyaluronic acid was dissolved in 50 ml of water to obtain a solution with a concentration 2 mg/mL and then neutralized to pH 6.5 with 0.1 M sodium hydroxide. 5 mg 2,2'(ethylenedioxy)bis(ethylamine) was dissolved in 2 ml of water and it was added to the hyaluronic acid solution. After the addition 20 mg of water soluble carbodiimide to the mixture, the reaction was stirred at 4° C. for 30 min and subsequently at ambient temperature for 24 hours. After this time the resulting solution containing hyaluronan nanoparticles was purified by dialysis for 7 days against distilled water and freeze dried.

EXAMPLE 5

Partial Cross-Linking of Hyaluronic Acid (50% of the Free Carboxylic Groups are Reacting)

100 mg hyaluronic acid was dissolved in 50 ml of water to obtain a solution, with a concentration 2 mg/mL and then neutralized to pH 6.5 with 0.1 M sodium hydroxide. 10 mg 2,2'(ethylenedioxy)bis(ethylamine) was dissolved in 2 ml of water and it was added to the hyaluronic acid solution. After the additional 40 mg of water soluble carbodiimide to the mixture, the reaction was stirred at 4° C. for 30 min and subsequently at ambient temperature for 24 hours. After this time the resulting solution containing hyaluronan nanoparticles was purified by dialysis for 7 days against distilled water and freeze dried.

EXAMPLE 6

Partial Cross-Linking of Hyaluronic Acid (50% of the Free Carboxylic Groups are Reacting 100 mg hyaluronic acid was dissolved in 50 ml of water to obtain a solution with a concentration 2 mg/mL and then neutralized to pH 6.5 with 0.1 M sodium hydroxide. 7 mg 2,5-diaminopyridine was dissolved in 2 ml of water and it was added to the hyaluronic acid solution. After the addition 40 mg of water soluble carbodiimide to the mixture, the reaction was stirred at 4° C. for 30 min and subsequently at ambient temperature for 24 hours. After this time the resulting solution containing hyaluronan nanoparticles was purified by dialysis for 7 days against distilled water and freeze dried.

EXAMPLE 7

Partial Cross-Linking of Hyaluronic Acid (80% of the Free Carboxylic Groups are Reacting)

100 mg hyaluronic acid was dissolved in 50 ml of water to obtain a solution with a concentration 2 mg/mL and then neutralized to pH 6.5 with 0.1 M sodium hydroxide. 12.5 mg 2,6-diaminohexane was dissolved in 5 ml of water and it was added to the hyaluronic acid solution. After the addition 64 mg of water soluble carbodiimide to the mixture, the reaction was stirred at 4° C. for 30 min and subsequently at ambient temperature for 24 hours. After this time the resulting solution containing hyaluronan nanoparticles was purified by dialysis for 7 days against distilled water and freeze dried.

EXAMPLE 8

Partial Cross-Linking of Hyaluronic Acid (50% of the Free Carboxylic Groups are Reacting)

100 mg hyaluronic acid was dissolved in 50 ml of water to obtain a solution with a concentration 2 mg/mL and then neutralized to pH 6.5 with 0.1 M sodium hydroxide. 40 mg of water soluble carbodiimide was dissolved in 5 ml of water After the addition of the CDI to the HA solution, the reaction was stirred at 4° C. for 30 min and subsequently at ambient temperature for 24 hours. After this time the resulting solution containing hyaluronan nanoparticles was purified by dialysis for 7 days against distilled water and freeze dried.

What is claimed is:

1. A process of making a cross-linked nanoparticle comprising reacting a linear polycarboxylic acid and an amino compound having at least two amino groups, said amino compound having the formula

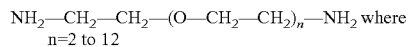
n=2 to 12 and a water soluble carbodiimide, said carbodiimide acting as a coupling agent for said carboxylic acid and said amino compound, said reaction being performed in a solution wherein the solvent consisting of water.

2. A process according to claim 1 wherein said polycarboxylic acid is hyaluronic acid.

3. A process according to claim 2 wherein said amine forms an amide linkage with said hyaluronic acid.

4. A process according to claim 3, wherein said reaction product is a a network of nanosized biocompatible and biodegradeable cross-linked particles.

5. A process according to claim 1, wherein said carbodiimide used as a coupling agent in the formation of the amide linkage between carboxyl and amino groups is 1-[3-(dimethylamino)propyl]-3-ethylcarbodiimide hydrochloride.

6. A process according to claim 5, wherein the particles formed by the reaction have an average diameter ranging from about 20 mm to about 200 mm.

7. A process according to claim 6, wherein said amine is a di, tri or polyamine.

8. A process according to claim 7, wherein there is about 1% to about 100% cross-linking.

9. A process of making a cross-linked nanoparticle comprising reacting a linear polycarboxylic acid and a 2,2'(ethylenedioxy)bis(ethylamine) and a water soluble carbodiimide, said carbodiimide acting as a coupling agent for said carboxylic acid and said amino compound, said reaction being performed in a solution wherein the solvent consisting of water.

10. A process according to claim 9 wherein said polycarboxylic acid is hyaluronic acid.

11. A process according to claim 10, wherein said reaction product is a a network of nanosized biocompatible and biodegradeable cross-linked particles.

12. A process according to claim 11, wherein the particles formed by the reaction have an average diameter ranging from about 20 mm to about 200 mm.

13. A process according to claim 12, wherein there is about 1% to about 100% cross-linking.

14. A process according to claim 1 wherein said amino compound is 1,3-diamino-2-hydropropane.

15. A process of making a cross-linked nanoparticle comprising reacting a linear polycarboxylic acid and an amino compound having at least two amino groups, said amino compound comprising an aromatic di/tri/polyamine and a water soluble carbodiimide, said carbodiimide acting as a coupling agent for said carboxylic acid and said amino compound, said reaction being performed in a solution wherein the solvent consisting of water.

16. A process according to claim 15 wherein said amino compound is 2,5-diaminobenzenesulfonic acid.

17. A process according to claim 15 wherein said amino compound is 3,5-diaminobenzoic acid.

18. A process according to claim 15 wherein said amino compound is 2,6-diaminopyridine.

19. A process according to claim 15 wherein said amino compound is 2,5-diaminopyridine.

20. A process according to claim 15 wherein said amino compound is 2,6-diaminopurine.

21. A process of making a cross-linked nanoparticle comprising reacting a linear polycarboxylic acid and an amino compound having at least two amino groups, said amino compound comprising an oxo-di/tri/polyamine and a water soluble carbodiimide, said carbodiimide acting as a coupling agent for said carboxylic acid and said amino compound, said reaction being performed in a solution wherein the solvent consisting of water.

22. A process according to claim 15 wherein said amino compound is 1,3-diaminoacetone.

23. A process of making a cross-linked nanoparticle comprising reacting a linear polycarboxylic acid and an amino compound having at least two amino groups, said amino compound comprising Poly-(ethylenglycol)-bis-(carboxymethylether) and a water soluble carbodiimide, said carbodiimide acting as a coupling agent for said carboxylic acid and said amino compound, said reaction being performed in a solution wherein the solvent consisting of water.

24. A process of making a cross-linked nanoparticle comprising reacting a linear polycarboxylic acid and an amino compound having at least two amino groups, said amino compound having the formula $H_2N-(CH_2)_n-NH_2$, where n=0 to 6 or $H_2N-(CH_2)_n-(CHOH)_m-NH_2$ where n=0 to 2 and m=0 to 2 and a water soluble carbodiimide, said carbodiimide acting as a coupling agent for said carboxylic acid and said amino compound, said reaction being performed in a solution wherein the solvent consisting of water.

* * * * *